United States Patent
Henderson, Sr. et al.

(10) Patent No.: US 8,043,342 B2
(45) Date of Patent: Oct. 25, 2011

(54) CRANIOSPINAL FUSION METHOD AND APPARATUS

(75) Inventors: Fraser Cummins Henderson, Sr., Upper Marlboro, MD (US); John W. Newman, Newtown Square, PA (US)

(73) Assignee: Polaris Biotechnology, Inc., Newtown Square, PA (US)

( * ) Notice: Subject to any disclaimer, the term of this patent is extended or adjusted under 35 U.S.C. 154(b) by 391 days.

(21) Appl. No.: 11/832,643

(22) Filed: Aug. 1, 2007

(65) Prior Publication Data

US 2008/0234766 A1 Sep. 25, 2008

Related U.S. Application Data

(60) Provisional application No. 60/887,022, filed on Jan. 29, 2007.

(51) Int. Cl.
*A61B 17/70* (2006.01)

(52) U.S. Cl. ........ 606/264; 606/265; 606/267; 606/272; 606/286

(58) Field of Classification Search ............ 606/61, 606/250–278, 280, 289, 315, 71, 290–297, 606/70, 86 B, 100, 281, 286, 288, 328, 903; 411/412, 413, 81, 87, 108, 355, 366.1, 389, 411/419, 779; 439/778, 791; 403/187, 256, 403/384, 398, 399
See application file for complete search history.

(56) References Cited

U.S. PATENT DOCUMENTS

| | | | | |
|---|---|---|---|---|
| 1,135,699 A | * | 4/1915 | Knauber | 174/63 |
| 1,750,769 A | * | 3/1930 | Austin | 248/226.12 |
| 3,073,022 A | | 1/1963 | Bush et al. | |
| 4,456,005 A | * | 6/1984 | Lichty | 606/60 |
| 4,653,481 A | * | 3/1987 | Howland et al. | 606/261 |
| 4,655,199 A | | 4/1987 | Steffee | |
| 4,762,122 A | | 8/1988 | Slocum | |
| 4,790,702 A | * | 12/1988 | Maganias | 411/412 |
| 4,800,874 A | | 1/1989 | David et al. | |
| 4,805,602 A | | 2/1989 | Puno et al. | |
| 5,030,220 A | | 7/1991 | Howland | |
| 5,034,011 A | | 7/1991 | Howland | |
| 5,129,900 A | * | 7/1992 | Asher et al. | 606/264 |

(Continued)

OTHER PUBLICATIONS

Grob, D., et al., 'Posterior Occipitocervical Fusion A Preliminary Report of a New Technique', Spine, vol. 16, No. 3 Supplement, Jan. 1, 1991, pp. S17-S24.

(Continued)

*Primary Examiner* — Thomas C. Barrett
*Assistant Examiner* — Christian Sevilla
(74) *Attorney, Agent, or Firm* — Knoble Yoshida & Dunleavy, LLC (57) ABSTRACT

A method for effecting reduction, stabilization and enhancement of fusion of the human cranio-cervical junction, which may be performed in order to relieve mechanical stresses imparted to the spinal cord and brainstem as a result of an abnormal clivo-axial angle, includes steps of achieving the correct craniocervical relationship, of effecting a fusion of a first portion of a bone forming material based structural member to a human cranium, and effecting fusion of a second portion of the bone forming material based structural member to a least one portion of a human cervical spine. Fusion of the bone forming material based structural member to the human cranium may be promoted through the use of plate member that is shaped to define a graft accommodation space between the plate member and the cranium.

20 Claims, 6 Drawing Sheets

U.S. PATENT DOCUMENTS

| | | | |
|---|---|---|---|
| 5,133,716 A | | 7/1992 | Plaza |
| 5,176,680 A | * | 1/1993 | Vignaud et al. ............... 606/302 |
| 5,269,784 A | | 12/1993 | Mast |
| 5,360,429 A | | 11/1994 | Jeanson et al. |
| 5,470,333 A | | 11/1995 | Ray |
| 5,507,745 A | | 4/1996 | Logroscino et al. |
| 5,545,164 A | | 8/1996 | Howland |
| 5,545,228 A | * | 8/1996 | Kambin ........................... 606/60 |
| 5,643,261 A | * | 7/1997 | Schafer et al. ................. 606/250 |
| 5,653,710 A | * | 8/1997 | Harle ............................. 606/308 |
| 5,733,285 A | * | 3/1998 | Errico et al. .................... 606/278 |
| 5,800,435 A | | 9/1998 | Errico et al. |
| 5,968,047 A | * | 10/1999 | Reed ............................... 606/76 |
| 6,039,738 A | * | 3/2000 | Sanders et al. .............. 606/86 A |
| 6,056,753 A | | 5/2000 | Jackson |
| 6,059,786 A | | 5/2000 | Jackson |
| 6,080,579 A | | 6/2000 | Hanley, Jr. et al. |
| 6,102,913 A | | 8/2000 | Jackson |
| 6,125,526 A | * | 10/2000 | Wierzchon ................ 29/525.02 |
| 6,129,728 A | | 10/2000 | Schumacher et al. |
| 6,129,730 A | * | 10/2000 | Bono et al. .................... 606/291 |
| 6,146,382 A | | 11/2000 | Hurlbert |
| 6,179,841 B1 | | 1/2001 | Jackson |
| 6,193,719 B1 | | 2/2001 | Gournay et al. |
| 6,221,073 B1 | | 4/2001 | Weiss et al. |
| 6,224,596 B1 | | 5/2001 | Jackson |
| 6,319,254 B1 | * | 11/2001 | Giet et al. ..................... 606/916 |
| 6,325,803 B1 | | 12/2001 | Schumacher et al. |
| 6,355,043 B1 | | 3/2002 | Adam |
| 6,423,067 B1 | | 7/2002 | Eisermann |
| 6,454,768 B1 | | 9/2002 | Jackson |
| 6,454,772 B1 | | 9/2002 | Jackson |
| 6,520,990 B1 | * | 2/2003 | Ray ............................. 623/17.11 |
| 6,524,315 B1 | | 2/2003 | Selvitelli et al. |
| 6,547,790 B2 | | 4/2003 | Harkey, III et al. |
| 6,565,566 B1 | | 5/2003 | Wagner et al. |
| 6,623,486 B1 | | 9/2003 | Weaver et al. |
| 6,726,687 B2 | | 4/2004 | Jackson |
| 6,761,721 B2 | | 7/2004 | Burgess et al. |
| 6,783,527 B2 | | 8/2004 | Drewry et al. |
| 6,902,565 B2 | | 6/2005 | Berger et al. |
| 6,928,900 B2 | | 8/2005 | Dall et al. |
| 6,997,927 B2 | | 2/2006 | Jackson |
| 7,018,379 B2 | | 3/2006 | Drewry et al. |
| 7,033,358 B2 | | 4/2006 | Taylor et al. |
| 7,052,499 B2 | | 5/2006 | Steger et al. |
| 7,131,303 B1 | | 11/2006 | Champaigne |
| 7,213,999 B2 | * | 5/2007 | Haas ............................. 403/337 |
| 7,235,079 B2 | | 6/2007 | Jensen et al. |
| 7,303,563 B2 | * | 12/2007 | Poyner et al. ................. 606/279 |
| 7,354,442 B2 | | 4/2008 | Sasso et al. |
| 7,537,596 B2 | * | 5/2009 | Jensen ........................... 606/280 |
| 2002/0120268 A1 | | 8/2002 | Berger |
| 2003/0153913 A1 | * | 8/2003 | Altarac et al. ................... 606/61 |
| 2003/0176863 A1 | * | 9/2003 | Ueyama et al. ................. 606/61 |
| 2004/0153070 A1 | | 8/2004 | Barker et al. |
| 2005/0038438 A1 | * | 2/2005 | Anderson et al. ............... 606/73 |
| 2005/0080417 A1 | | 4/2005 | Alexis et al. |
| 2005/0124994 A1 | * | 6/2005 | Berger et al. .................... 606/61 |
| 2005/0143737 A1 | * | 6/2005 | Pafford et al. ................... 606/61 |
| 2005/0216001 A1 | * | 9/2005 | David ............................... 606/61 |
| 2005/0283153 A1 | * | 12/2005 | Poyner et al. .................... 606/61 |
| 2005/0283248 A1 | | 12/2005 | Gordon et al. |
| 2005/0288669 A1 | | 12/2005 | Abdou |
| 2006/0004363 A1 | | 1/2006 | Brockmeyer et al. |
| 2006/0079895 A1 | * | 4/2006 | McLeer .......................... 606/61 |
| 2006/0173543 A1 | * | 8/2006 | Brau et al. ................. 623/17.11 |
| 2006/0217710 A1 | * | 9/2006 | Abdou ............................ 606/54 |
| 2007/0118121 A1 | * | 5/2007 | Purcell et al. .................... 606/61 |
| 2008/0039843 A1 | | 2/2008 | Abdou |
| 2008/0086124 A1 | | 4/2008 | Forton et al. |
| 2008/0125781 A1 | | 5/2008 | Hoffman et al. |

OTHER PUBLICATIONS

Sandhu, Faheem A., MD, PhD, et al., "Occipitocervical Fusion for Rheumatoid Arthritis Using the Inside-Outside Stabilization Technique", SPINE, 2003, pp. 414-419, vol. 28, No. 4.

Kim, Louis J., M.D., et al., "Treatment of basilar invagination associated with Chiari I malformations in the pediatric population: cervical reduction and posterior occipitocervical fusion", J. Neurosurg: Pediactrics, 2004, pp. 189-195, vol. 101.

Grabb, Paul A., M.D., et al., "Ventral Brain Stem Compression in Pediatric and Young Adult Patients with Chiari I Malformations", Neurosurgery, 1999, pp. 520-528, vol. 44, No. 3.

Tassanawipas, A. et al., "Magnetic resonance imaging study of the craniocervical junction", Journal of Orthopaedic Surgery, 2005, pp. 228-231, vol. 13, No. 3.

Kumar, Raj et al., "Management of Pediatric Congenital Atlantoaxial Dislocation: A Report of 23 Cases from Northern India", Pediatric Neurosurgery, 2002, pp. 197-208, vol. 36.

Goel, Atul, M.Ch., "Treatment of basilar invagination by atlantoaxial joint distraction and direct lateral mass fixation" J. Neurosurg: Spine, 2004, pp. 281-286, vol. 1.

Henderson, Fraser C., M.D., et al., "Stretch-Associated Injury in Cervical Spondylotic Myelopathy: New Concept and Review" Neurosurgery, 2005, pp. 1101-1113, vol. 56, No. 5.

* cited by examiner

CRANIOSPINAL FUSION METHOD AND APPARATUS

BACKGROUND OF THE INVENTION

1. Field of the Invention

The present invention relates to a method and apparatus for fixation, stabilization and fusion of the human occipitocervical junction.

2. Description of the Related Technology

The normal range of motion of the craniospinal junction includes 27° of flexion and extension, and 90° of lateral rotation; the craniospinal junction is thus the most mobile and articulatable part of the human body. It is also the most active part of the human body in movement throughout the day, typically performing greater than 3 million motions a year. The craniospinal junction transmits the entire nervous structure to the body (with the exception of the vagus nerve), and is thus unfortunately susceptible to a host of degenerative disorders. Emblematic of these is rheumatoid arthritis, a chronic degenerative condition that arises in 2% of the population, causing predictable changes in the joints and bone structure of the cervical spine, often including vertical migration of the odontoid and trauma to the ligamentous structures of the craniocervical junction.

25% of rheumatoid arthritis sufferers develop atlantoaxial subluxation and 9% develop basilar invagination. Clinically these patients invariably experience severe neck pain and neurological deficits, including weakness and sensory loss. Untreated, patients suffer progressive decline, losing the ability to walk. The untreated patient with myelopathy due to compression of the spinal cord has a 50% likelihood of dying within 1 year. Surgical intervention is therefore necessary to stabilize the craniocervical junction, restore neurologic function and prevent further neurologic deterioration. However, occipitocervical stabilization in rheumatoid arthritis can be especially challenging because of such factors as poor bone quality, poor nutritional status and long term steroid use.

There are also other common causes of cranio-cervical instability, including traumatic fractures, which can include approximately 3,000 fractures of the upper spine related to head trauma each year; congenital diseases, including Down's, Morquio's and spondyloepiphyseal dysplasia syndromes, with a prevalence of at least 50,000; osteogenesis imperfecta, with a prevalence of 7,000 patients; cancer, with about 1000 cases per year; and numerous causes of bone softening. Tumors and infections may also cause destruction of the stabilizing elements.

However, the largest group of patients suffering from poor craniocervical stabilization lies in the pediatric group amongst a large group of children who have been misdiagnosed with neuropsychiatric disorders, such as Asperger's Syndrome, autism, Attention Deficit Hyperactivity Disorder and forms of dyslexia who harbor underlying disorders of the brainstem and spinal cord which result from subtle and sometimes gross anomalies which result in mechanical deformation and abnormal stresses of the neuraxis at the craniocervical junction. Various disorders have been found to frequently result in chronic and subtle neurological changes: retroflexion of the odontoid, platybasia, non-traditional forms of basilar invagination and an abnormal clivo-axial angle, which can result in deformity of the brainstem and upper spinal cord.

Figure 1:
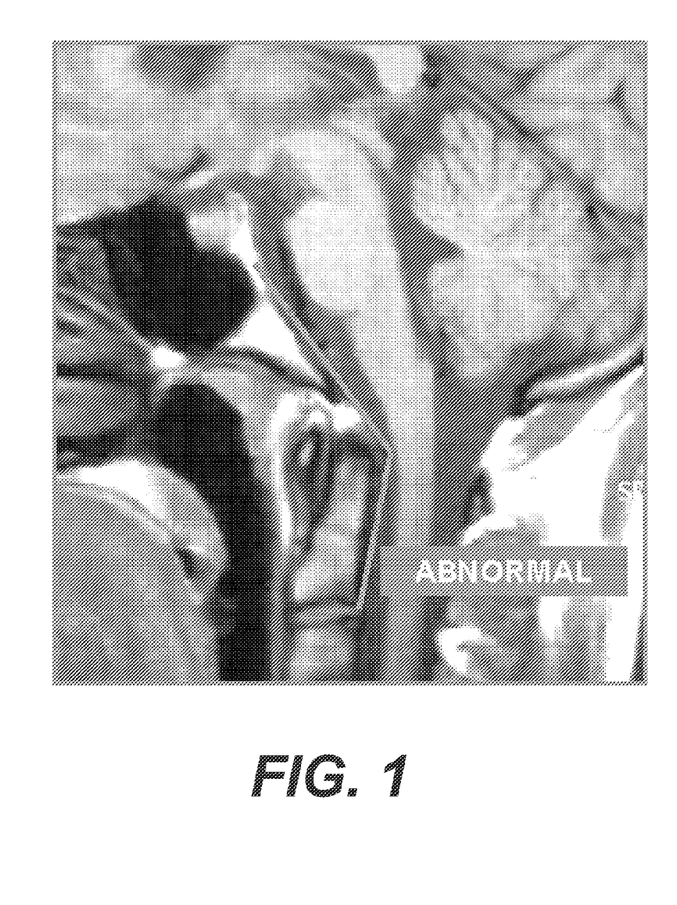
FIG. 1 is an image depicting the clivo-axial angle in a human, with an abnormal clivo-axial angle being shown.
Figure 2:
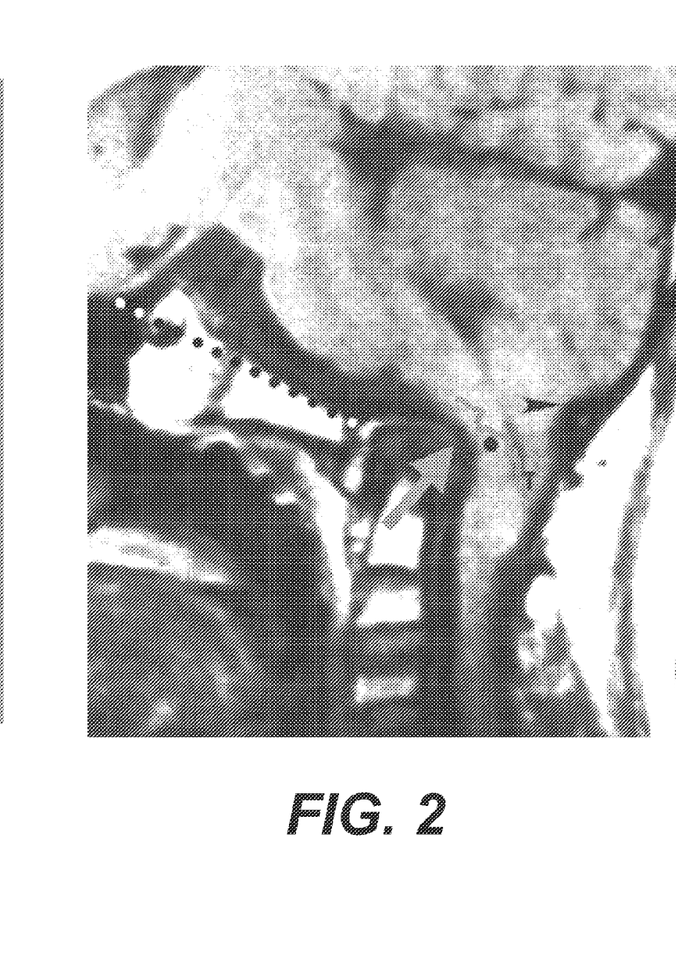
FIG. 2 is an annotated image depicting compression of the brainstem as a result of an abnormal clivo-axial angle in a human.

The clivioaxial angle is depicted in FIG. 1, while an example of basilar invagination is depicted in the image that is shown in FIG. 2, with compression to the brainstem being clearly visible. These conditions have been reported to cause such symptoms as sleep apnea, delayed speech, gastroesophageal reflux, and altered behavior such as attention deficit disorder, headaches, and a myriad of other sensori-motor syndromes. The ubiquity of craniospinal junction pathology has only recently been appreciated.

Hitherto, patients undergoing craniospinal stabilization have required an arduous surgery and recovery. Some patients undergo a decompressive surgery from the front of the neck (transoral resection of the uppermost part of the spine), followed by fusion in the back of the neck, and followed by 3 months of stabilization in a halo brace, which encompasses the head (held by 4 screws in the skull) and the upper body.

Numerous fixation devices have been described such as those that are disclosed in U.S. Pat. Nos. 5,030,220; 5,034,011; 5,545,164; 5,507,745; 6,547,790; 6,524,315; 6,902,565 B2 and U.S. Published Patent Applications US2005/0288669 A1; US2005/0283153 A1 and US2005/0080417 A1, all of which are hereby incorporated by reference as if set forth fully herein.

A need exists for a system and methodology that accomplishes the goals of reduction of deformity, successful immobilization and fusion of the craniospinal junction, in a shortened surgery, thereby allowing the patient to return to a normal quality of life within a short period of time.

SUMMARY OF THE INVENTION

Accordingly, it is an object of the invention to provide a system and methodology that accomplishes the goals of reduction of deformity, successful immobilization and fusion of the craniospinal junction, in a shortened surgery, thereby allowing the patient to return to a normal quality of life within a short period of time. In order to achieve the above and other objects of the invention, a method for effecting fusion of the human occipitocervical junction according to a first aspect of the invention includes steps of effecting fusion of a first portion of a bone forming material based structural member to a human cranium; and effecting fusion of a second portion of the bone forming material based structural member to a least one portion of a human cervical spine, whereby a fusion of the human occipitocervical junction is achieved.

An article for use in the surgical fusion of the human occipitocervical junction according to a second aspect of the invention includes a plate member having an outer edge, an outer surface and an inner surface that is constructed and arranged to be secured to a human cranium, the plate member being configured so as to define a graft accommodation space between the inner surface of the plate member and the cranium when the plate member has been secured to the cranium, the graft accommodation space being defined in part by a portion of the outer edge that is elevated with respect to a portion of the inner surface that is contacting the cranium so that the graft accommodation space is open to a space outside of the graft accommodation space, whereby a bone material based structural member may be positioned within the graft accommodation space so as to be fused to the cranium and to extend away from the plate member.

A system according to a third aspect of the invention for fusing a bone material based structural member to a human cranium includes a plate member, the plate member being constructed and arranged to securely position a bone material based structural member against a human cranium, the plate member having at least one threaded hole defined therein; a rod member, the rod member having a hole defined therein; a triple screw member that is sized to fit within said hole that is defined in the rod member, the triple screw member having a first threaded portion for engaging the threaded hole in the plate member, a second threaded portion for engaging the human cranium and a third threaded portion; and a nut member secured to the third threaded portion, whereby the nut member may be tightened in order to secure the rod member, the plate member in the cranium and desired relative positions so as to promote fusion of said bone material based structural member to the human cranium.

A system for effecting fusion of the human occipitocervical junction according to a fourth aspect of the invention includes a first bone material based structural member that is positioned so as to facilitate fusion of a first portion thereof to a human cranium and a second portion thereof to a cervical vertebral body; a second bone material based structural member that is positioned so as to facilitate fusion of a first portion thereof to a human cranium and a second portion thereof to a cervical vertebral body; and a transverse connector that is positioned to compress the first bone material based structural member and the second bone material based structural member against a vertebral body.

According to a fifth aspect of the invention, a system for effecting fusion of the human occipitocervical junction includes surgically implantable instrumentation including a first support rod; a second support rod; cranium attachment means for attaching respective first portions of the first and second support rods to a human cranium; vertebral attachment means for attaching respective second portions of the first and second support rods to a human cervical vertebral body; and wherein the first and second support rods are contoured to ensure a postoperative craniospinal angle that is within a range of about 80° to about 90°.

A system for effecting fusion of the human cranio-cervical junction according to a sixth aspect of the invention includes surgically implantable instrumentation preferably including cranium attachment structure for attaching to a human cranium; two appendages that are integral with the cranium attachment structure; vertebral attachment structure for attaching respective second portions of the first and second appendages to a human cervical vertebral body; and wherein the first and second appendages are contoured to ensure a postoperative clivo-axial angle of about 155° to about 165°.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

The present invention relates to a system and method for stabilizing and fusing the human craniospinal junction. The technology is predicated upon the importance of first, reduction of the deformity at the craniospinal junction, and second of providing the surface area available for and the mileau most conducive to formation of bone fusion. It accomplishes the latter by providing greater bone surface available for bone fusion, and through application of load to the graft. The technology involves fewer steps to apply, therefore provides for faster application, and shorter surgery with respect to conventional processes.

Figure 3:
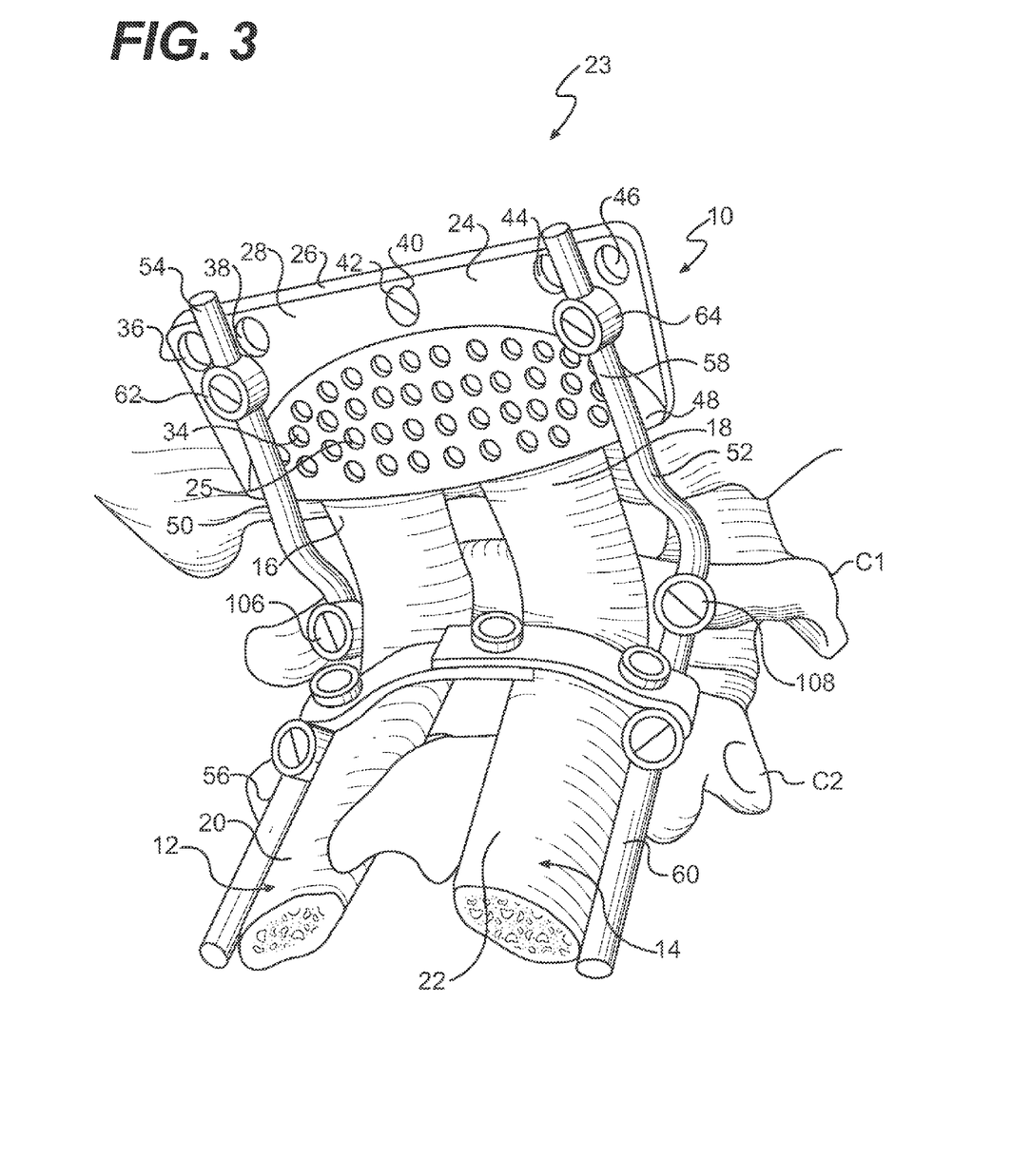
FIG. 3 is a fragmentary perspective view of a system for effecting fusion of the human occipitocervical junction according to a preferred embodiment of the invention.

Referring now to the drawings, wherein like reference numerals designate corresponding structure throughout the views, and referring in particular to FIG. 3, a system 10 for use in the surgical fusion of the human occipitocervical junction according to a preferred embodiment of the invention includes a first bone forming material based structural member 12 and a second bone forming material based structural member 14.

The two bone forming material based structural members 12, 14 may be bone grafts that are harvested from another part of the patient's body, such as a rib, grafts from a cadaver, or a material that is constructed and arranged to facilitate the growth of bone. The invention is accordingly not limited to bone, but may use bone substitutes or non-osseous materials to accomplish long-term fixation of the cranium to the spine. For example, the two bone forming material based structural members 12, 14 may be fabricated from a metallurgically bonded porous metal coating that is constructed and arranged to encompass and contain bone graft material, such as the material that is marketed under the trade name TRABECULAR METAL by Zimmer Inc. of Warsaw, Ind.

The two bone forming material based structural members 12, 14 could alternatively be fabricated from a bone forming material such as a bone substitute that is fabricated from a collagen base and contains bone forming materials, or bone enhancing chemicals. Thus a bone forming material could be embodied as a fabricated mesh that functions as a bone conductor (that a form into which bone growth would occur, or as a bone-like medium such as coralline hydroxyapatite, which serves as an osteoconductor for blood vessel formation and subsequent deposition of bone, which could be injected or poured into the space between the bones to be fused.

Alternatively, the bone forming material could be embodied as a metallic mesh-like substance that encourages or enables bone growth, such as tantalum mesh, which could be molded to fit into the space between the occiput and the spine, a bone allograft or a xenograft.

The first bone forming material based structural member 12 has a first portion 16 that is positioned and biased against the cranial bone so as to promote bone fusion between the cranial bone and the first bone forming material based structural member 12. Accordingly, the second bone forming material based structural member 14 has a first portion 18 that is positioned and biased against the cranial bone so as to promote bone fusion between the cranial bone and the second bone forming material based structural member 14. In the preferred embodiment, these functions of positioning, support, biasing and promotion of fusion are effected through the use of the unique occipital connection system 23, which will be described in greater detail below.

The bone forming material based structural members 12, 14 preferably each have transverse cross-sectional area of approximately 1 cm$^2$.

The first and second bone forming material based structural members 12, 14 further respectively have second portions 20, 22 that are positioned and biased against at least one cervical vertebral body of a human cervical spine so as to promote bone fusion between the cervical vertebral body and the respective bone forming material based structural member 12, 14. In the preferred embodiment, this function is effected through the use of the unique vertebral connection system 100, which will be described in greater detail below. Preferably, the system 10 facilitates a fusion between said bone forming material based structural members 12, 14 and both the C1 and C2 cervical vertebral bodies.

Figure 4:
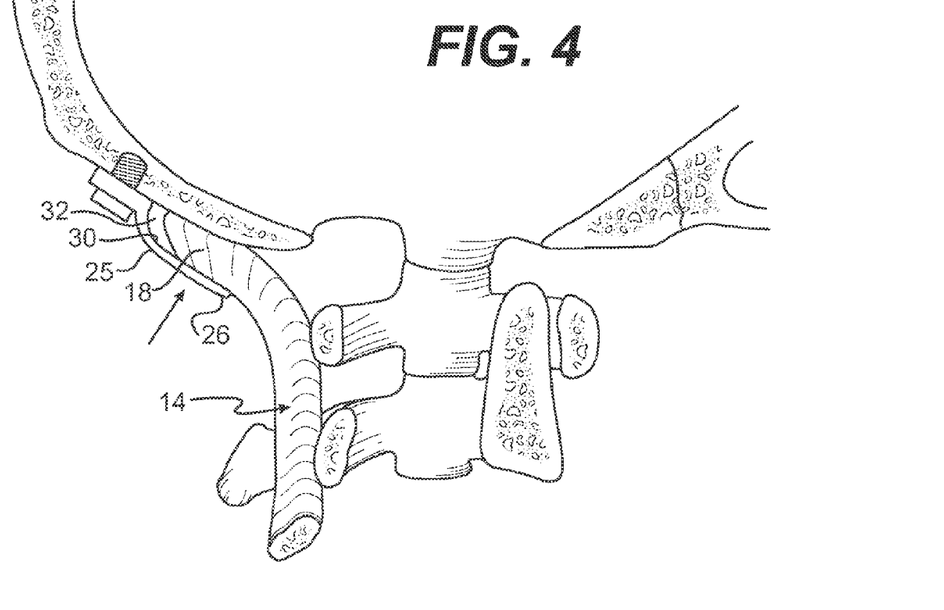
FIG. 4 is a fragmentary cross-sectional view of a portion of the system that is depicted in FIG. 3.

In the preferred embodiment, the inseparable connection system 23 includes a plate member 24 that is shaped so as to define an outer edge 26, an outer surface 28 and an inner surface 30, as is best shown in FIG. 4. Plate member 24 is preferably shaped to define a graft accommodation space 32 between the plate member 24 and the cranium. The graft accommodation space is preferably defined in part by a flange 25 defined in the plate member 24 by a portion of the plate member 24 including the caudal portion of the outer edge 26 that is elevated away from the cranium with respect to a portion of the inner surface 30 that is contacting the cranium so that the graft accommodation space 32 is open to a space outside of the graft accommodation space 32. As clearly shown in FIG. 4, the inner surface of flange 25 is substantially parallel to and spaced part from the cranium, defining a graft accommodation space between the inner flange surface and the cranium when the plate member has been secured to the cranium.

The plate member 24 is preferably a monolithic plate, composed of metal, poyetheretherketone (PEEK), bio-absorbable compound, bone or bone substitute. The plate member 24 preferably has a thickness of more than 1 mm and less than 1 cm at the edges, and may vary in thickness. For instance the plate edge 26 may be 1 mm, but the central part may be increased to 15 mm. The plate member 24 may be ovoid, rectangular, polyhedral or a composite of straight edges and curves, and thus is not confined to a particular shape or perimeter. The plate member 24 may be coated or made of a bio-compatible material, or coated with substances which are known to improve or accelerate surface attachment, or to promote bone fusion. The plate member 24 may or may not contain a metallurgically bonded porous metal coating. The plate member 24 may be slightly curved so as to be complementary to the curve of the cranium, or may be flat, or may undergo a contouring process by the surgeon or assistant at the time of surgery.

The flange 25 is an elevated contour arising from the plate member 24. The flange 25 makes available for fusion the underlying cranial surface; the elevation of the flange 25 exposes the cranial bone surface to the overlying bone graft. The flange 25 may be constructed from the same material as the remainder of the plate member 24, or it may be a constructed as a separate component that is attachable to the plate member 24. The purpose of the flange 25 is to incorporate, to enclose or to provide a fulcrum in which bone graft materials or substitutes, or other materials, may be held for the purpose of achieving a bone union or other permanent rigid or non-rigid attachment between the cranium and the spine.

The flange 25 may be non-perforate, or single or multiply perforate, and could be composed of a mesh or mesh-like construction. The flange 25 is preferably perforated to allow in-growth of bodily tissue or blood vessels. The flange has a perforated plus non-perforated surface area of more than 15% of the area of the plate component.

The thickness of the flange 25 is 0.5 to 5 mm thickness. The purpose of the flange 25 is to entrap the bone forming substances or other structural members in close union with the underlying cranium, and to facilitate in the case of bone, morphogenesis through application of load; that is, through pressure and stabilization of the bone forming substances to enhance the milieu favoring new bone formation. The flange 25 may have a facility to be mechanically altered in shape to further compress the graft.

The flange 25 will preferably rise from the plane of the portion of the plate member 24 that contacts the cranial bone for a distance that is more than about 5 mm, to allow placement of a thickness of material that is adequate to provide stability for growth. It is envisioned that malleable, or woven-bone forming substrates could be used to promote fusion, or indeed provide the scaffolding itself for fusion. Conversely, other materials could be used beneath the flange 25 to provide non-osseous, non-rigid fixation.

Flange 25 will preferably allow the passage or inset of rods, plates or other materials for connecting the cranial plate to the spine. The purpose of this is to lower the profile of the rod, and to minimize the potential deformity of overlying tissue. Thus, a rod may pass through a perforation in a mesh of the flange to connect to the triple screw. Alternately, the flange may have a groove, a pop-out section or possess the faculty of perforability to allow passage of the stabilization element connecting cranium to spine.

In an alternative embodiment, the flange 25 might serve to provide attachment for a non-osseous union between the cranium and spine. The flange 25 thus may have both a physiological function and a mechanical function.

Flange 25 is envisioned in the preferred embodiment to arise from the lower aspect of the plate member 24. However, alternate embodiments would allow positioning of a single or multiple flanges in various locations, such as the middle, the upper or the sides of the plate. Thus the flange should not be construed to exist only as an elevation from the lower edge of the plate, but, for instance, may be centered on the plate; a rim of plate could thus fully encompass the flange(s).

Whilst the preferred embodiment of the flange 25 is curved to minimize profile by conforming to anatomic contour, alternate forms may include box-like constructs, or even a multiplicity of shapes and sizes that could be chosen for a given application, and then be secondarily attached to the plate. For example, a low profile, curved flange could be applied to the plate over the cranium of an asthenic child where the thickness of skin and muscle contraindicate thickness of construct; another embodiment, for a larger person, may be a larger box-like adaptation designed to facilitate the incorporation of a more rectanguloid, synthetic bone-forming substance or other non-osseous compound. It is thus envisioned that a multiplicity of options to accomplish different goals in persons (or other species of animal) of different morphology.

As is shown in FIG. 4, the first portion 18 of the second bone material based structural member 14 is preferably positioned within the graft accommodation space 32 defined by the flange 25 so that the inner surface 30 of the plate member 24 is biased to provide compressive pressure against the second bone material based structural member 14. This compression will facilitate bone fusion between the second bone material based structural member 14 and the cranium.

As FIG. 3 shows, the first portion 16 of the first bone material based structural member 12 is similarly positioned within the graft accommodation space 32 and impressively biased against the cranial bone to promote bone fusion.

Alternatively, the plate member 24 could be fabricated so as to include more than one graft accommodation space, so that each of the two structural members 12, 14 could be separately positioned within different accommodation spaces that are defined by the inner surface 30 of the plate member 24.

The inner surface 30 of the plate member 24 is preferably composed of a material that promotes fusion to bone. This could be accomplished by coating the plate member 24 with anyone of a number of conventional bone growth promoting substances or by fabricating the plate member 24 from a porous material that is constructed and arranged to encompass and contain bone graft material, such as the TRABECULAR METAL material described above. Plate member 24 further preferably has a plurality of perforations 34 defined therein. Perforations 34 preferably have a minimum diameter of at least 400 microns, so as to best facilitate the growth of blood vessels within the newly formed bone tissue. A portion 48 of the outer surface 28 of the plate member 24 may be grooved in order to accommodate instrumentation, as will be described in greater detail below.

Plate member 24 preferably has a plurality of pre-drilled threaded mounting holes 36, 38, 40, 44, 46, 72 defined therein for facilitating attachment of the plate member 24 to first portions 54, 58 of first and second support rods 50, 52 by means of first and second fastening assemblies 62, 64, respectively. The plate member 24 will therefore preferably include manifold screw holes in order to permit the support rods 50, 52 to be secured to the plate member 24 and locations that are most suitable for an individual patient.

A central screw hole 40 will serve to anchor a central plate screw 42. There may be multiple 'central screw' holes. The central screw hole(s) lie(s) approximately in the midline of the patient's body and cranium in order to permit placement of screw(s) into the thickest part of the skull, which usually runs from the inion to the opisthion. These holes may be threaded, partially threaded or not threaded. On each side of the midline, additional holes 38, 44, 46, 72 will be positioned to receive additional screws, called the triple screws 70.

The triple screws 70 engaged in the plate will serve to anchor the stabilization elements (rods, plates or other) from the cervical spine. These holes may be single or multiple; the holes may cluster, may overlap, may be placed in an arc, or contiguously or in separately locations. The holes may be placed around the edge of the flange, or on the flat portion of the plate. These holes may be reinforced with extra thickness, and may be threaded or not. Second portions 56, 60 of the first and second support rods 50, 52 are secured to the cervical spine of the patient, as will be described in greater detail below.

The central plate screw 42 provides primary attachment of the plate to the skull. It is robust, cortically threaded, of variable length, preferably having a month within a range of about 7 mm to about 12 mm. The central plate screw 42 preferably has a thickness within a range of about 2 mm to about 10 mm, with a blunted end. It may have a spiral lock feature that locks the screw 42 into the plate member 24, or not. It may be lagged to provide increased loading pressure on the plate member 24, or not. It can be made of titanium alloy, of bone, or of a bone forming or bone compatible substance. For example, a ceramic, or hydroxyl-apatite composite or metal alloy/bone composite could be used.

In an alternative embodiment, a screw/rivet could be used in lieu of the central plate screw 42 for rapid application. The screw or screw/rivet would preferably have torque strength of greater than 35 inch lb and generate sufficient pullout strength to prevent dislodgement from the cortex. The screw or screw/rivet would be placed near the middle of the plate member 24, and be fashioned to pass through the central screw hole 40 on the plate member 24.

The first and second support rods 50, 52 provide the main structural connection between the cranium and the upper cervical spine during the immediate postoperative period. Support rods 50, 52 are preferably standard titanium rods, approximately of 3-4 mm gauge, bent to conform to the correct craniospinal angle. The salient differences from other rods currently available are two-fold. The first is an angle reflecting the corrected reduction of the angle ($\alpha$ angle, FIG. 9) between the cranium and that of the spine; in the preferred embodiment this will be pre-set within a range of about 75° to about 90°. Accordingly, the first and second support rods are contoured to ensure a postoperative craniospinal relationship that confers a clivo-axial angle (the angle between the dorsum of the second cervical vertebra and the dorsum of the clivus) approaching about 145-165°, and more preferably about 155 to 165°. Simultaneously, the degree of ventral brainstem compression should be rendered close to zero, by virtue of the reduction of angulation between the cranium and spine, and in some cases by the posterior translation of cranium upon spine.

Second, the craniospinal support rods 50, 52 will have a pre-established rise option (the $\beta$ rise, FIG. 9), to accommodate the non-linearity of the level of the posterior ring of the first cervical vertebra C1 to the surface of the lamina of C2 and lateral mass of C3. Accordingly, the presence of the pre-established $\beta$ rise will allow the support rods 50, 52 to contact the C1 and C2 laminae.

Figure 5:
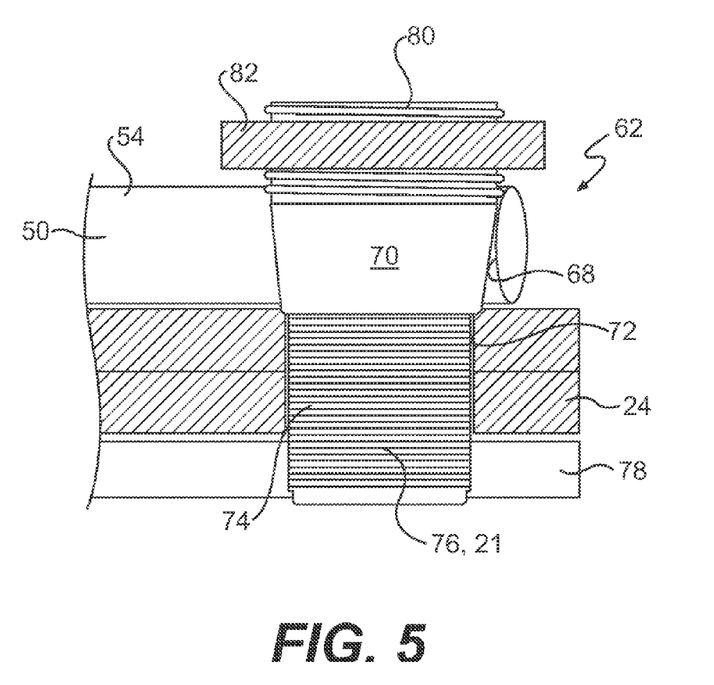
FIG. 5 is a fragmentary cross-sectional view depicting a fastening assembly that is constructed according to a preferred embodiment of the invention.

Fastening assembly 62 is shown in greater detail in FIG. 5. In the preferred embodiment, an unthreaded hole 68 is defined in the first portion 54 of the first support rod 50 and a threaded hole 72 is provided in the plate member 24. Fastening assembly 62 advantageously includes a unique triple screw 70 that has a first threaded portion 70 at an intermediate section thereof that is sized and pitched to mate with the threaded hole 72 in the plate member 24 and a second threaded portion 76 at a lower section thereof that is constructed and arranged to be screwed into the cranial bone 78.

Triple screws 70 have the unique characteristic of deriving stability from fixation within the skull, the plate member 24 and around the rod or plate that connects the cranium to the spine. In addition, the triple screw 70 is tri-purposive: first, it connects the plate to the cranium; second, it connects the cranium to the craniospinal connecting devices; third, it eliminates plate torque around the central screw 42. In so doing, it eliminates one of the steps common to all other craniospinal devices: that of an additional and independent means of attaching the plate member 24 to the craniospinal rod or plate connector.

Triple screws 70 are so-called because they possess three functional portions of the screw length: a threaded portion for attachment to the cranial bone 78, a threaded, or non threaded, portion to engage the plate member 24, and a threaded portion for attaching the support rod 50. The central or intermediate portion may be threaded to enhance binding to the plate member 24, or non-threaded to allow a lag effect upon the plate member 24, in order to allow the insertion of the screw to tighten the plate down to the cranial bone 78, depending upon the requirements of the particular stabilization.

The triple screws 70 may be placed in one of many potential screw holes on each side of the plate member 24, in order to accommodate to the variability of the system that attaches the cranium to the cervical spine. Whilst the triple screws 70 are shown in the upper portion of the plate in the illustrated embodiment, they may in another embodiment be placed in the lower aspect of the plate. They are not limited to being positioned at lateral opposite sides of the plate member 24, but may be placed near the middle of the plate member 24. The triple screw 70 can be turned to any direction to accommodate the craniospinal rod or connector system.

The triple screw 70 will preferably be inserted through the plate and screwed into the skull. The triple screw 70 will provide increased stability to the plate and rod system by virtue of the combined fixation of the screw within the plate and the skull. The triple screw 70 may be threaded at the level of the skull with a cortical or cancellous thread, or could in another embodiment utilize a rivet-type fixation. In any event, the internal portion of the screw is firmly fixated to the skull.

Triple screw 70 further includes a third threaded portion 80 at an upper portion thereof that is sized in pitch to mate with an internally threaded hexagonal nut 82. As is shown in FIG. 6, which provides a top plan view of an alternative fastening assembly 62 including a hole positioned through the width of triple screw 70 below nut 82 for receiving, engaging and retaining the first support rod 50, an upper surface of the triple screw 70 is provided with a slot for receiving a screwdriver blade.

Figures 6, 7, 8, 9:
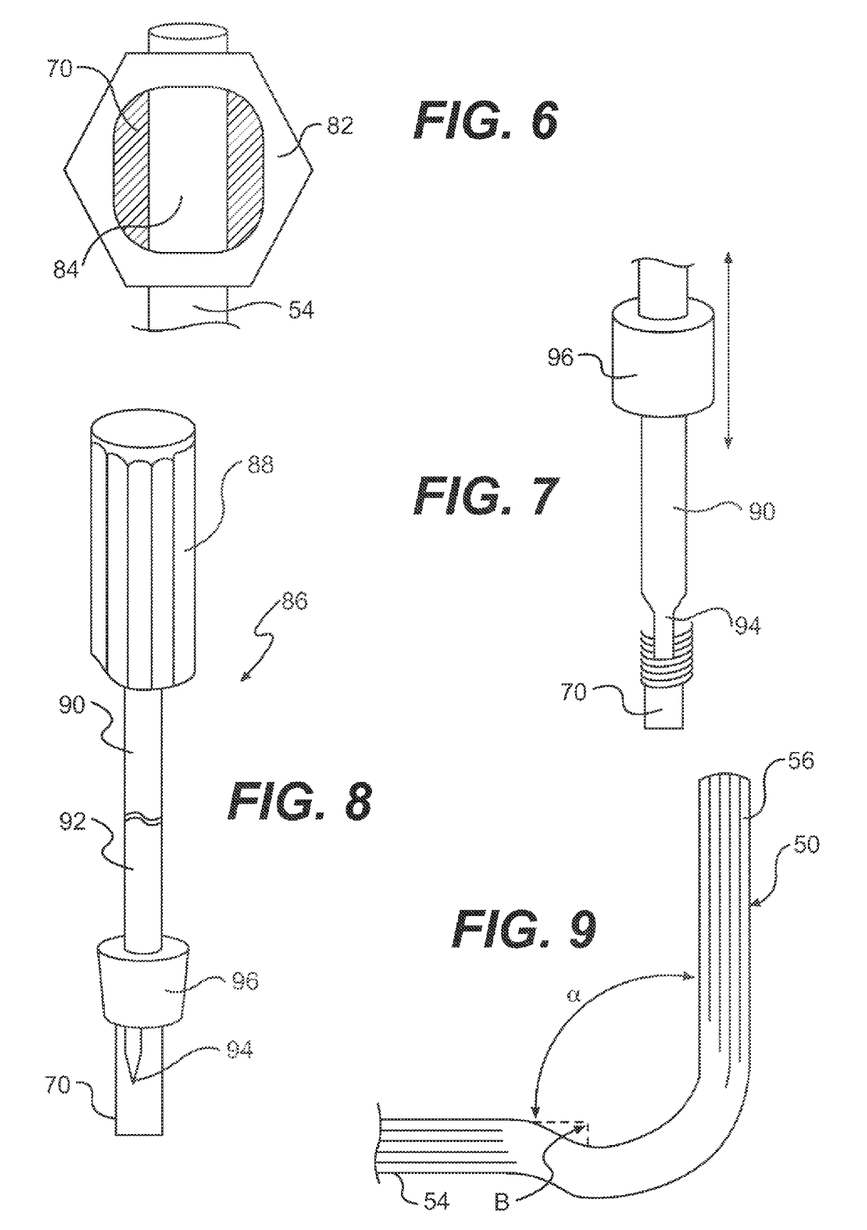
FIG. 6 is a fragmentary top plan view of another fastening assembly.
FIG. 7 is a diagrammatical depiction of a fastening tool that is designed to be used in conjunction with the fastening assembly that is depicted in FIG. 5, shown in a first operative position.
FIG. 8 is a diagrammatical depiction of the fastening tool that is shown in FIG. 7, shown in a second operative position.
FIG. 9 is a fragmentary side elevational view of one component of the system that is depicted in FIG. 3.

FIGS. 7 and 8 depict a unique tool 86 that is constructed and arranged to be used in conjunction with the fastening assembly 62 and the triple screw 70. Tool 86 includes a handle 88 and a shaft 90 that may be provided with a universal joint 92 for accessibility purposes, e.g. to accommodate non-orthogonal placement of the screw. For instance, if access to the triple screw 70 is encumbered by a patient's corpulence, the screw may be inserted at an angle. A screwdriver blade 94 is provided at a distal end of the shaft 90 and is preferably sized and shaped to be effectively received by the slot 84 that is defined in the upper surface of the triple screw 70. Additionally, tool 86 preferably includes a sleeve 96 that is slidable upwardly and downwardly on the lower portion of the shaft 90 between a first retracted position that is shown in FIG. 7 and a second, extended operative position that is shown in FIG. 8. Sleeve 96 is shaped to define an internally threaded socket that mates with the external thread 80 of the triple screw 70. Sleeve 96 is further mounted to the shaft 90 so that it is prevented from rotating with respect to the shaft 90. Accordingly, a surgeon may use the tool 86 in the operative position that is shown in FIG. 7 in order to tighten the triple screw 70 with respect to the plate member 24 and the cranial bone 78 with the sleeve 96 stabilizing the tool 86 with respect to the triple screw 70 and preventing the blade 94 from slipping out of the slot 84.

Figure 10:
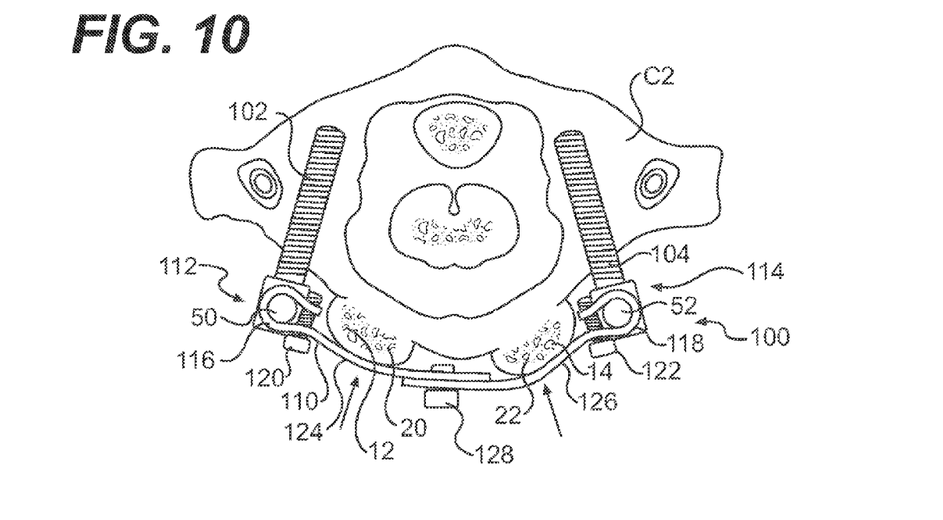
FIG. 10 is a cross-sectional view depicting certain components of the system that is shown in FIG. 3.
Figure 11:
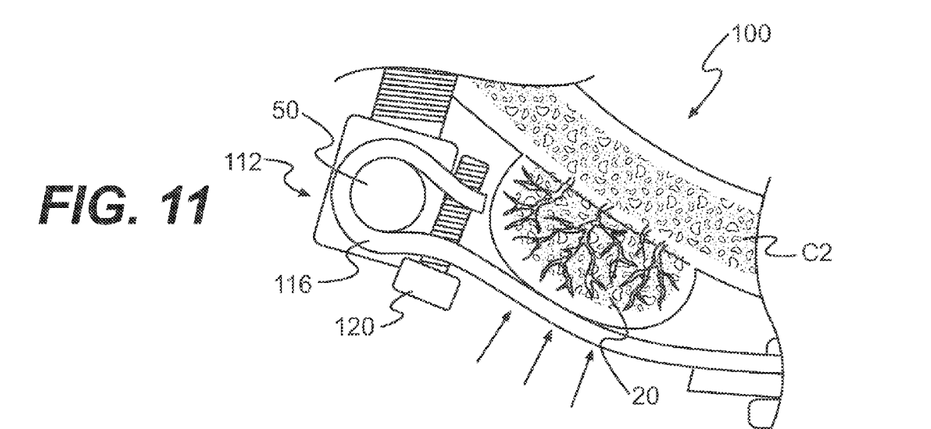
FIG. 11 is a fragmentary cross-sectional view depicting certain components of the portion of the system shown FIG. 3 that is depicted in FIG. 10.
Figure 12:
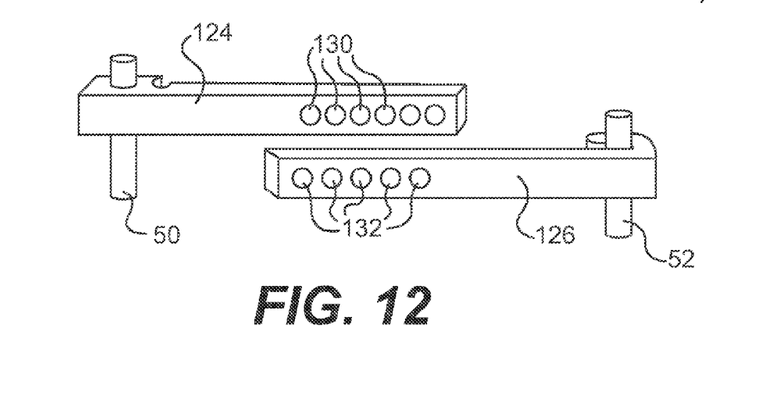
FIG. 12 is a diagrammatical depiction of certain components of the portion of the system that is shown in FIG. 10.

Referring now to FIGS. 10-12, system 10 further includes a unique vertical connection system 100 for positioning and biasing the second portions 20, 22 of the first and second bone forming material based structural members 12, 14 against at least one cervical vertebral body of a human cervical spine so as to promote bone fusion between the cervical vertebral body and the respective bone forming material based structural member 12, 14.

In the preferred embodiment, the vertebral connection system 100 includes a transverse connector 110 that is positioned to compress the first bone material based structural member 20 and the second bone material based structural member 22 against a vertebral body such as the vertebral body C2 that is depicted in FIG. 10. The transverse connector 110 serves several purposes. First, the transverse connector 110 holds the graft material (the bone, bone substitute or other non-osseous material) into close contact, and usually under pressure, with the underlying spinal vertebrae, to facilitate in-growth of blood vessels or other tissue, as is dramatically depicted in FIGS. 10 and 11. Second, the transverse connector 110 stabilizes the two sides of the system 10, connecting the respective support rods 50, 52 from one side to that of the other, thereby decreasing the potential for toggling.

Accordingly, the transverse connector 110 is connected to the first structural support rod 50 at one portion thereof that includes a first clamping structure 112 for releasably clamping one end of the transverse connector 110 to the first structural support rod 50. In the preferred embodiment, the first clamping structure 112 includes a curved plate portion 116 that curves about most of the circumference of a first structural support rod 50. A screw 120 extends through first and second holes that are defined in the curved plate portion 116 for tightening and loosening the first clamping mechanism 112 with respect to the first structural support rod 50.

Likewise, the transverse connector 110 is connected to the second structural support rod 52 at a second portion thereof that includes a second clamping mechanism 114 for releasably clamping a second, opposite end of the transverse connector 110 to the second structural support rod 52. The second clamping structure 114 includes a curved plate portion 118 that curves about most of the circumference of the second structural support rod 52. A screw 122 extends through first and second holes that are defined in the curved plate portion 118.

The curved plate portions 116, 118 of the respective clamping mechanisms 112, 114 preferably extend around the circumference of the respective support rod 50, 52 as viewed in transverse cross-section for an angular distance of at least three radians. In addition, the clamping screws 120, 122 are preferably positioned on the medial side of the respective support rod 50, 52.

The transverse connector 110 is preferably curved so as to be concave on a side thereof that is positioned to contact the first bone material based structural member 20 and said second bone based structural member 22.

The transverse connector 110 further preferably includes structure for permitting adjustment of a length of the transverse connector 110, whereby a lateral spacing distance between said first and second laterally spaced structural support rods may be adjusted. In the preferred embodiment, this is accomplished by constructing the transverse connector 110 out of two separate components that are attachable to each other, specifically a first curved connector portion 124 and a second curved connector portion 126, as is best shown in FIG. 12.

The first connector portion 124 has a plurality of adjustment holes 130 defined therein while the second connector portion 126 similarly has a plurality of adjustment holes 132 defined therein. A top-loading screw member 128, which is best shown in FIG. 10, is provided for securing the first connector portion 124 to the second connector portion 126 and is preferably applied centrally in a precise manner in order to stabilize the first and second connector portions 124, 126. Screw member 128 is preferably although not necessarily a lock screw having a snap off head. A Vernier scale option may be used to generate the best precise fit, but other adaptations may be used, with the most important requirement being that a secure fit is created.

The graft loading transverse connector component arms 124, 126 are preferably curved, and may possess a plurality of curve sizes to accommodate the specific graft or implanted material size. In one possible alternative embodiment, the transverse connector arms are straight with a rise to accommodate the underlying material.

The surgically implantable instrumentation of the system 10 that has been described above, including the plate member 24 the support rods 50, 52 and the transverse connector 110 may alternatively be fabricated from a bioabsorbable material that progressively loses its strength and mass over time as it is absorbed into the human body. The ideal bioabsorbable material would have a composition that would retain sufficient strength for a sufficient period of time for adequate bone fusion and bone mass to develop so that the first and second bone forming material based structural members 12, 14 would provide adequate structural strength to maintain the fusion of the human occipitocervical junction at all times and under all foreseeable circumstances.

Figure 13:
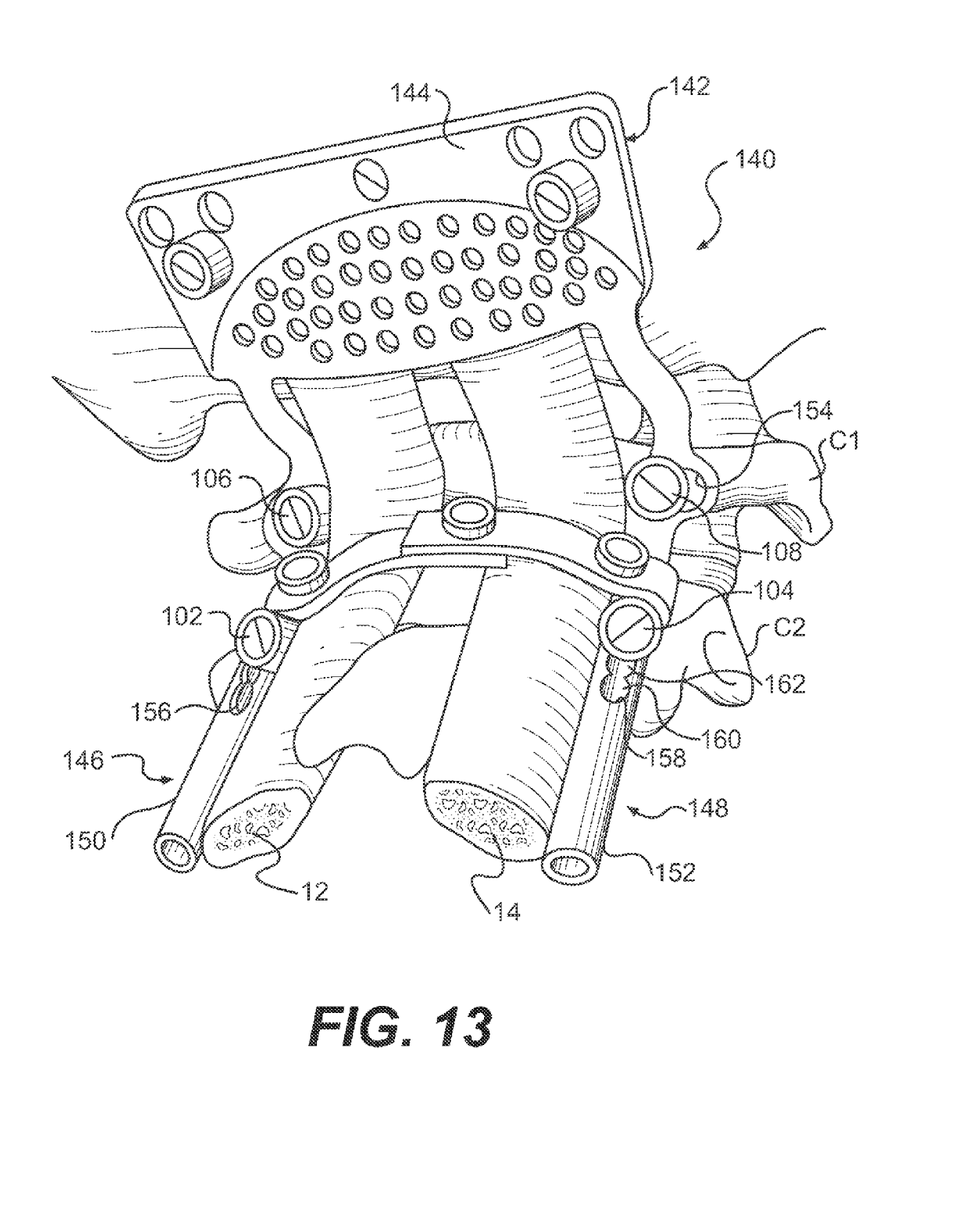
FIG. 13 is a fragmentary perspective view of a system for effecting fusion of the human occipitocervical junction according to alternative embodiment of the invention.

Referring now to FIG. 13, a system 140 that is constructed according to an alternative embodiment of the invention includes an integrated fixation member 142 having a plate portion 144 and first and second appendages 146, 148 that are integral and preferably unitary with the plate portion 144. The appendages 146, 148 would intimately relate to the posterior ring of C1 (the first vertebra and the lateral mass of C2, C3 and to any of the lower vertebrae, even as low as the thoracic vertebrae The goal of the monolithic design would be to simplify and increase the efficiency of application and stabilization of the device to the craniospinal junction.

Plate portion 144 is preferably constructed identically to the plate portion described above with reference to the previously described embodiment except as is described otherwise herein. The first and second appendages 146, 148 are preferably rigid and in the preferred embodiment are fabricated from a pair of generally parallel extending rod members 150, 152. Appendages 146, 148 are preferably preformed as described above with reference to the first embodiment of the invention so as to be bent at an angle reflecting the corrected reduction of the angle (α angle, FIG. 9) between the cranium and that of the spine, which in the preferred embodiment this will be pre-set within a range of about 75° to about 90°. Accordingly, the first and second integrated appendages 146, 148 are contoured to ensure a postoperative craniospinal relationship that confers a clivo-axial angle (the angle between the dorsum of the second cervical vertebra and the dorsum of the clivus) approaching about 155-165° and more preferably about 155-165°. Simultaneously, the degree of ventral brainstem compression should be rendered zero, by virtue of the reduction of angulation between the cranium and spine, and in some cases by the posterior translation of cranium upon spine.

In addition, the integrated appendages 146, 148 preferably incorporate a pre-established rise option (the β rise, described above with reference to FIG. 9), to accommodate the non-linearity of the level of the posterior ring of the first cervical vertebra C1 to the surface of the lamina of C2 and lateral mass of C3. The presence of the pre-established β rise will allow the integrated appendages 146, 148 to contact the C1 and C2 laminae, as shown in FIG. 13.

Another advantageous feature of the embodiment of the invention that is depicted in FIG. 13 is the provision of adjustment slots 156, 158 in the first and second appendages 146, 148, respectively, to permit positional adjustment of the integrated fixation member 142 with respect to the pedicle screws 102, 104 that are used to secure the first and second appendages 146, 148, respectively, to the C2 vertebrae. As FIG. 13 shows, adjustment slot 158 as well as adjustment slot 156 may include a plurality of prepositioned apertures or adjustment holes 160, 162 to permit indexing of the pedicle screw 104 within the appendage 148 or variability of screw purchase.

Likewise, adjustment slots 154 may be provided in the respective portions of the first and second appendages 146, 148 that are constructed and arranged to be secured to the C1 vertebrae by pedicle screws 106, 108. This portion of the appendages 146, 148 is preferably constructed so as to be slightly flared at the C1 vertebrae to allow lateral variability.

As may be visualized from viewing FIG. 13, several possibilities of latitude are offered for the screw heads at C1, and several options for the screw heads of C2 are also available. The appendages 146, 148 may be solid, tubular, porous or even a metallurgically bonded porous metal coating that is constructed and arranged to encompass and contain bone graft material, such as the material that is marketed under the trade name TRABECULAR METAL by Zimmer Inc. of Warsaw, Ind.

A method for achieving occipitocervical fusion according to a preferred embodiment of the invention will now be described. The patient is first positioned prone with a Mayfield pin headrest in an appropriate sterile surgical environment. The posterior cranium (subocciput) will then be surgically exposed.

The suboccipital bone will then preferably be lightly drilled or sculpted in order to create a flat and even surface for the positioning of the plate member 24. The plate member 24 will then be aligned with the long axis of the patient's body and will be positioned symmetrically about the midline axis, so that the central screw hole 40 is preferably bisected by the midline axis of the patient's cranium as viewed in rear elevation. The center of the central screw hole 40 will then be marked on the cranium, and the plate member 24 will be removed.

A central hole will then be surgically drilled in the cranium, preferably to a depth of 5-10 mm. using a high speed drill, then by a conventional surgical hand drill to complete the drilling, preferably to a total depth of between about 8 mm to about 12 mm. The screw hole will be tapped to a depth that is about 1 mm. longer than the screw to be used. (For example, for a 10 mm screw, tap to 11 mm depth). The plate member 24 will then be repositioned on the midline.

The central cortical screw 42 will then be inserted into the tapped hole and tightened, lagging down the plate member 24 to achieve solid fixation.

The left C1 and C2 screws 102, 106 will then be respectively inserted into the C1 and C2 vertebral bodies as is best shown in FIGS. 3 and 10.

The left pre-contoured support rod 50 is loosely positioned within the first clamping mechanism on 12 of the transverse connector 110 and is secured to the left C1 and C2 screws 102, 106.

The triple screw position for the first fastening assembly 62 that best aligns with the pre-contoured occipito-cervical rod 50 is then selected. The triple screw purchase selected is then drilled in the cranium. The lateral screw purchase may then be tapped if it is not been pre-threaded. The triple screw 70 is inserted.

The same operation is performed, again choosing the most appropriate position for the triple screw for the second fastening assembly 64.

The Mayfield headholder is then released, and an open reduction of the craniocervical junction is performed under fluoroscopy and under direct inspection. It is ensured that the abnormal angulation (kyphosis) of the craniospinal angle, and any abnormal translation of the skull is reduced, and that there is no rotation or lateral bending and no subluxation at lower spinal levels. The head-holder is then relocked.

The clivioaxial angle is then measured with the goal of achieving an optimal clivioaxial angle of 150° to 165°.

The support rods 50, 52 are then placed into the holes in triple screws 70 within the respective fastening assembly 62, 64 and the hex nuts 82 are placed over the screws 70 and tightened, as shown in FIG 6.

The exposed suboccipital bone, the posterior ring of C1 and the lamina and facet joints of C2 are then surgically decorticated.

The first portions 16, 18 of the first and second bone forming material based structural member 12, 14 are then inserted into the graft accommodation space 32 that is defined between the plate member 24 and the cranium, as is best shown in FIG. 4. The cephalad part of the bone forming material based structural member should be fashioned to fit precisely and under pressure beneath the flange 25 of the plate member 24. In some embodiments, the caudal edge 26 of the plate member 24 may now be bent down towards the cranium to further compress the graft. The caudal end of the graft should lie on the decorticated C1 and C2 (and lower levels where indicated) dorsal elements.

The graft loading transverse connector is then positioned to hold down, under pressure, the portions of the first and second bone forming material based structural members 12, 14 that are positioned over and against the C1 and C2 dorsal elements. This is best illustrated in FIGS. 10 and 11.

The locking screws 120, 122 are then tightened on the transverse connector.

Demineralized bone matrix may then be applied to the fusion areas and more cancellous bone may be applied to complete the fusion. A layered wound closure is then performed conventionally over a drain.

A method according to an alternative embodiment of the invention would utilize the integrated fixation member 142 that is depicted in FIG. 13. In this method, the preferred steps are preferably slightly reordered. First, placement of the screws into the lateral mass or ring or C1 and into the lateral mass or pedicle of C2, or into the lateral masses of the lower cervical or thoracic vertebrae would be performed.

Second the monolithic construct including the plate portion 144 and the integrated appendages 146, 148, which are surrogates for the rods 56 and 58 described with reference to the first embodiment of the invention, is applied over the screw heads.

Third, the craniospinal reduction is performed.

Fourth, the plate portion 144 is screwed to the skull 23 with the central screw 42. The top loading nuts 106, 108 are then tightened down over the screw heads of the vertebral screws.

In all other respects, this method is identical to the method first described above.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of part within the principles of the invention to the full extent indicated by the broad general meaning of the terms in which the appended claims are expressed.

What is claimed is:

1. A system for effecting fusion of the human craniocervical junction, comprising:
    a plate member, said plate member being constructed and arranged to securely position a bone forming material against a human cranium, said plate member having a hole defined therein, wherein said hole is defined by a threaded inner surface of the plate member and is configured as cylindrical through hole;
    a rod member;
    a triple screw member positioned within said hole, wherein said triple screw member comprises:
        a first portion that is inserted within said hole so as to directly contact a surface of said plate member defining said hole, wherein said first portion is threaded and has a cylindrical configuration that engages said threaded inner surface of the plate member;
        a second portion comprising a threaded surface capable of engaging the human cranium;
        a third portion comprising a threaded surface;
        wherein said rod member is received within and positioned through a width of said triple screw member; and
    a nut member secured to said third portion, wherein said rod member is secured below said nut member, and whereby said nut member may be tightened in order to fix said rod member and said plate member relative to said triple screw member and the cranium, such that said plate member adjoins said second portion and such that said rod member directly contacts said nut member.

2. A system according to claim 1, wherein said system comprises two of said rod members, two of said triple screw members and two of said nut members, and wherein said plate member has more than one hole defined therein, whereby attachment between said members and the human cranium may be made in more than one location.

3. A system for effecting fusion of the human craniocervical junction, comprising:
    surgically implantable instrumentation comprising:
    a first support rod;
    a second support rod;
    a plate member for attaching respective first portions of said first and second support rods to bone, wherein said plate member comprises a hole defined by a threaded inner surface of the plate member, wherein said hole is configured as cylindrical through hole; and
    a triple screw attachment means for attaching said first portion of said first support rod and said plate member to said bone without requiring an independent means for attaching said plate member to said first support rod, wherein said triple screw attachment means is inserted within and directly contacts the threaded inner surface of the plate member defining said cylindrical through hole and wherein said triple screw attachment means directly engages said first support rod such that an upper or lower surface of said first support rod is clamped by and directly contacts a surface of said triple screw attachment means, wherein said upper or lower surface faces a direction aligned with a length of said triple screw attachment means, wherein said triple screw attachment means is capable of engaging the bone while contacting the plate member and while said first support rod is clamped by and directly contacts said surface of said triple screw attachment means.

4. A system according to claim 3, wherein each of said first and second support rods incorporate a βrise to allow the first and second support rods to contact the C1 and C2 laminae.

5. A system according to claim 3, further comprising a transverse connector that is connected to said first and second support rods for providing lateral stability and spacing to said first and second support rods.

6. A system according to claim 3, wherein said first and second support rods are configured so that there is substantially no ventral brainstem compression and craniospinal junction deformity is reduced.

7. A system according to claim 3, wherein an angle between a first portion of said first and second support rods and the second portion of said first and second support rods is about 75° to about 90°.

8. A system according to claim 1, wherein said second portion comprises a cortical thread, cancellous thread or a rivet-type fixation.

9. A system according to claim 1, wherein said triple screw member is positioned in a region of said plate member selected from the group consisting of: an upper portion of said plate member, a lower aspect of said plate member, a lateral side of said plate member, and a middle region of said plate member.

10. A system according to claim 1, wherein an inner surface of said plate member is composed of a material that promotes fusion to bone.

11. A system according to claim 10, wherein said material comprises a metallurgically bonded porous metal coating that is constructed and arranged to encompass and contain bone forming material.

12. A system according to claim 1, wherein said plate member comprises a plurality of perforations.

13. A kit for use in effecting fusion of the human cranio-cervical junction, comprising:
a triple screw member adapted to be surgically implanted in bone, wherein said triple screw member comprises:
a first portion sized to engage a plate, wherein said first portion has a cylindrical configuration and a threaded surface adapted for directly contacting a surface of said plate defining a threaded cylindrical through hole;
a second portion comprising a threaded surface for engaging bone;
a third portion comprising a threaded surface on an exterior surface thereof;
a nut member secured to said third portion, whereby said nut member comprises a threaded surface on an interior surface thereof and wherein said nut member is fitted over and screwed onto said third portion in order to secure a rod;
wherein said rod is received within and is positioned through a width of said triple screw member adjoining said first portion and below said nut member, wherein said triple screw member is capable of being surgically implanted in a body and attached to said bone, and wherein said triple screw member is adapted to fix said plate and said rod to said bone, such that said plate adjoins said second portion and such that said rod directly contacts said nut member.

14. A kit according to claim 13, wherein said threaded surface of said second portion is selected from the group consisting of a cortical thread and cancellous thread.

15. A system according to claim 1, wherein said a triple screw member consists essentially of said first portion, said second portion, said third portion and said nut member.

16. A system according to claim 1, wherein said rod member engages said triple screw member between said first portion and said third portion.

17. A system according to claim 1, wherein said first portion is positioned between said second and third portions such that said plate member is positioned adjacent to said rod member.

18. A kit according to claim 13, further comprising a tool for securely attaching said triple screw member to said bone, wherein said tool comprises:
a shaft;
a screwdriver blade positioned at a distal end of said shaft; and
a sleeve adapted to be slidably positioned relative to said shaft, wherein said sleeve comprises a internally threaded socket adapted to mate with a threaded exterior surface of said third portion of said triple screw member and wherein said sleeve secures said screwdriver blade to said nut.

19. A kit according to claim 18, wherein said sleeve is mounted to said shaft so as to be slidably position along the length of said sleeve wherein said sleeve is rotatably fixed relative to said shaft.

20. A system for stabilizing the human cranio-cervical junction, consisting essentially of:
one or more support rods;
one or more plates, wherein said one or more plates have a continuous inner surface with exception of one or more holes formed therein, wherein a surface of said one or more plates that forms said one or more holes are threaded and wherein the continuous inner surface is adapted to be placed against and conform to a contour of a bone surface; and
one or more triple screw attachment means for attaching said one or more support rods and said one or more plates to said bone surface without requiring an independent means for attaching said one or more plates to said one or more support rods, wherein said triple screw attachment means is positioned within one of said one or more holes and wherein said triple screw attachment means directly contacts and engages said one or more support rods and said bone surface wherein said one or more triple screw attachment means includes a first threaded portion that engages said one or more holes, a second threaded portion capable of engaging the human cranium, and a third threaded portion that engages a threaded nut member.

* * * * *